US012807585B2

(12) United States Patent
Jacquin et al.

(10) Patent No.: US 12,807,585 B2
(45) Date of Patent: Nov. 24, 2026

(54) METHOD FOR PRODUCING A HIGH-PURITY AQUEOUS 5-HYDROXYMETHYLFURFURAL (5-HMF) SOLUTION

(71) Applicant: IFP ENERGIES NOUVELLES, Rueil-Malmaison (FR)

(72) Inventors: Marc Jacquin, Rueil-Malmaison Cedex (FR); Maria Fernandez Espada Pastor, Rueil-Malmaison Cedex (FR); Kim Larmier, Rueil-Malmaison Cedex (FR); Helene Lorcet, Rueil-Malmaison Cedex (FR); Thi Bich Ngoc Dang, Rueil-Malmaison Cedex (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 271 days.

(21) Appl. No.: 18/723,000

(22) PCT Filed: Dec. 6, 2022

(86) PCT No.: PCT/EP2022/084588
§ 371 (c)(1),
(2) Date: Jun. 21, 2024

(87) PCT Pub. No.: WO2023/117407
PCT Pub. Date: Jun. 29, 2023

(65) Prior Publication Data

US 2025/0051297 A1 Feb. 13, 2025

(30) Foreign Application Priority Data

Dec. 23, 2021 (FR) ....................................... 2114337

(51) Int. Cl.
*C07D 307/48* (2006.01)
*B01D 11/04* (2006.01)

(52) U.S. Cl.
CPC ............ *C07D 307/48* (2013.01); *B01D 11/04* (2013.01)

(58) Field of Classification Search
CPC .............................. C07D 307/48; B01D 11/04
USPC .......................................................... 549/489
See application file for complete search history.

(56) References Cited

U.S. PATENT DOCUMENTS 8,338,626 B2 12/2012 Gruter et al.
10,829,463 B2 11/2020 Jacquin et al.

FOREIGN PATENT DOCUMENTS

FR 2669635 A1 5/1992
WO 2019052937 A1 3/2019

OTHER PUBLICATIONS

International Search report PCT/EP2022/84588 dated Feb. 6, 2023 (pp. 1-2).

*Primary Examiner* — Kristin A Vajda
(74) *Attorney, Agent, or Firm* — Millen, White, Zelano & Branigan, PC; Brion P. Heaney

(57) ABSTRACT

The invention relates to a process for producing an aqueous solution of 5-hydroxymethylfurfural (5-HMF), comprising:

a step a) of placing a feedstock comprising 5-HMF and dimethyl sulfoxide (DMSO) in contact with an intermediate aqueous back-extract obtained from step c), to obtain an aqueous mixture, a step b) of liquid-liquid extraction of the aqueous mixture with a stream of extraction solvent, to produce an aqueous raffinate and an intermediate organic extract, a step c) of back-washing of the intermediate organic extract with an aqueous solvent, to produce the intermediate aqueous back-extract and an organic raffinate, a step d) of liquid-liquid back-extraction of the organic raffinate obtained on conclusion of step c) with an aqueous stream, to produce an organic effluent and an aqueous back-extract of 5-HMF.

21 Claims, 1 Drawing Sheet

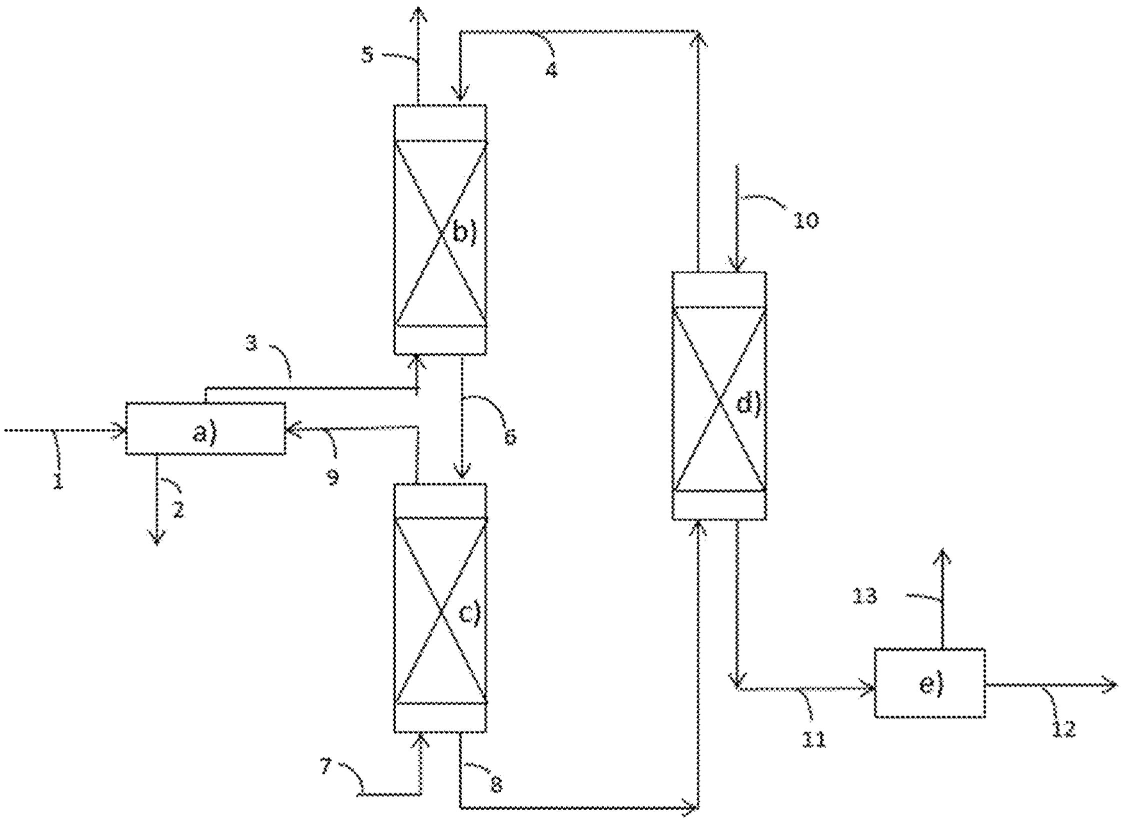
a)
b)
c)
d)
e)
1
2
3
4
5
6
7
8
9
10
11
12
13

METHOD FOR PRODUCING A HIGH-PURITY AQUEOUS 5-HYDROXYMETHYLFURFURAL (5-HMF) SOLUTION

TECHNICAL FIELD

The invention relates to a process for producing a high-purity aqueous solution of 5-hydroxymethylfurfural (5-HMF).

PRIOR ART

5-HMF is an advantageous compound resulting from biomass, which can be exploited in many fields, notably in pharmaceuticals, agrochemistry or specialty chemistry. The production of 5-HMF by dehydration of sugars has been known for many years and has formed the subject of a large number of research studies. There are numerous dehydration conditions, and mention may notably be made, by way of example, of the following methods:

- 5-HMF can be obtained in aqueous medium, generally in the presence of an acid catalyst. This acid catalyst makes it possible to dehydrate the C6 sugar (in particular fructose) to give 5-HMF, but also catalyzes the rehydration of 5-HMF to give formic acid and levulinic acid, which is very harmful to the yield.
- 5-HMF can also be obtained in nonaqueous polar protic medium, with solvents such as methanol, ethanol or acetic acid, and in the presence of an acid catalyst. Under these conditions, 5-HMF is obtained as a mixture with an ether or ester derivative of 5-HMF, depending on the reaction medium used. The formation of these byproducts is due to the reaction of 5-HMF with the reaction solvent in acidic medium. Patent application WO 2007/104514 describes the synthesis of 5-HMF by dehydration of sugar using methanol or ethanol as solvent in the presence of an acid catalyst. In this case, the presence of said catalyst also catalyzes the etherification reaction of 5-HMF with the alcohol to give a mixture of 5-HMF and of its methyl or ethyl ether form, depending on the alcohol used as solvent.
- 5-HMF can also be produced in polar aprotic medium, with or without an acid catalyst. Mention may more particularly be made of the use of dimethyl sulfoxide (DMSO) which, with or without an acid catalyst, makes it possible to produce 5-HMF in very good yields, and without the undesirable reactions listed above.

Furthermore, whatever the synthesis medium (water, methanol, DMSO, and the like), polymeric byproducts called humins are formed during the production of 5-HMF (van Dam, H. E.; Kieboom, A. P. G.; van Bekkum, H. (1986), The Conversion of Fructose and Glucose in Acidic Media: Formation of Hydroxymethylfurfural, In: Starch-Stärke, vol. 38, No. 3, pages 95-101).

The synthesis of 5-HMF in a medium such as DMSO is particularly advantageous, as it makes it possible to obtain 5-HMF in its alcohol form (rather than the ether form) in very good yields. Nevertheless, the physicochemical properties of DMSO (or any other polar aprotic solvent) make it very difficult to separate from 5-HMF by the usual methods known to those skilled in the art.

One known method for isolating 5-HMF from DMSO is liquid-liquid extraction, followed by crystallization of the extract, as described in patent FR 2 669 635. The Applicant has already proposed an improvement to the process described in patent FR 2669635, which was the subject of patent FR 1758605. This improvement is based on modifying the extraction step, notably by adding a water back-washing step, and recycling the back-washing water into the optional filtration step. This improvement allows the purity of 5-HMF to be increased without loss of yield of the product of interest, and allows the 5-HMF crystallization step to be performed under more favorable conditions.

Nevertheless, despite the improvements afforded by patent FR 1758605, 5-HMF crystallization remains a costly operation. The high production cost of 5-HMF limits its use, and the development of a cost-saving process is necessary.

The Applicant has discovered a process which allows 5-HMF to be recovered not in crystallized form but in aqueous solution, opening up new possibilities for the exploitation of 5-HMF in various applications, or for further transformations which could not be performed either in DMSO or in the extraction solvent. Moreover, the process according to the invention thus allows 5-HMF to be recovered in aqueous solution, while at the same time limiting the operating costs, water discharges and hence the environmental impact of the process.

SUMMARY OF THE INVENTION

One subject of the present invention relates to a process for producing a high-purity aqueous solution of 5-HMF.

More particularly, the invention relates to a process for producing an aqueous solution of 5-hydroxymethylfurfural (5-HMF), said process comprising the following steps:

- a step a) of placing a feedstock comprising 5-HMF and dimethyl sulfoxide (DMSO) in contact with at least a fraction of an intermediate aqueous back-extract advantageously obtained from step c), so as to obtain at least one aqueous mixture,
- a step b) of liquid-liquid extraction of the aqueous mixture obtained on conclusion of step a) in the presence of a stream of extraction solvent, so as to produce an aqueous raffinate and an intermediate organic extract,
- a step c) of back-washing of the intermediate organic extract with an aqueous solvent, so as to produce the intermediate aqueous back-extract and an organic raffinate 8 which comprises 5-HMF and an organic solvent,
- a step d) of liquid-liquid back-extraction of the organic raffinate obtained on conclusion of step c) with an aqueous stream, so as to produce an organic effluent and an aqueous back-extract.

The process for producing an aqueous solution of 5-HMF may optionally also comprise a step e) of concentrating the aqueous back-extract obtained from step d) by elimination of an aqueous effluent, to produce a concentrated aqueous solution comprising 5-HMF. Optionally, it also comprises a step f) of treating the water-DMSO mixtures produced within the process, to produce a treated aqueous effluent, which may be used totally or partly in the back-washing step c), and/or in the back-extraction step d).

DESCRIPTION OF THE EMBODIMENTS

It is specified that, throughout this description, the expression "between . . . and . . . " should be understood as including the limits mentioned.

For the purposes of the present invention, the various embodiments presented may be used alone or in combination with each other, without any limit to the combinations.

For the purposes of the present invention, the various ranges of parameters for a given step, such as the pressure ranges and the temperature ranges, can be used alone or in combination.

For example, for the purposes of the present invention, a preferred range of pressure values can be combined with a more preferred range of temperature values.

For better understanding of the invention, numerical references appearing in the appended FIGURE are mentioned below to denote various elements of the process, without this constituting a limitation to the invention or to the particular embodiment illustrated in FIG. 1 and described in detail further below.

Optional Step of Sugar Dehydration

Advantageously, the feedstock 1 comprising 5-HMF and dimethyl sulfoxide (DMSO) introduced in step a) according to the invention can be obtained during a step of sugar dehydration to 5-HMF, very advantageously located upstream of step a) according to the invention, by placing a sugar feedstock comprising one or more sugars in contact with DMSO and an acidic dehydration catalyst so as to produce an effluent comprising at least 5-HMF and DMSO and advantageously corresponding to the feedstock 1 of the process according to the invention introduced in the mixing step a). The process according to the invention may thus optionally comprise a step of sugar dehydration to 5-HMF, located upstream of step a).

The term "acidic dehydration catalyst" means any Brønsted acid catalyst chosen from organic or inorganic, homogeneous or heterogeneous Brønsted acids which can induce the dehydration of sugars to 5-HMF.

Preferably, the acidic dehydration catalyst is a Brønsted acid with a pKa in DMSO of between 0 and 5.0, preferably between 0.5 and 4.0 and more preferably between 1.0 and 3.0. Said pKa values are as defined in the article by F. G. Bordwell et al. (*J. Am. Chem. Soc.,* 1991, 113, 8398-8401).

Preferably, the acidic dehydration catalyst is chosen from HF, HCl, HBr, HI, $H_2SO_3$, $H_2SO_4$, $H_3PO_2$, $H_3PO_4$, $HNO_2$, $HNO_3$, $H_2WO_4$, $H_4SiW_{12}O_{40}$, $H_3PW_{12}O_{40}$, $(NH_4)_6(W_{12}O_{40})\cdot xH_2O$, $H_4SiMO_{12}O_{40}$, $H_3PMo_{12}O_{40}$, $(NH_4)_6Mo_7O_{24}\cdot xXH_2O$, $H_2MoO_4$, $HReO_4$, $H_2CrO_4$, $H_2SnO_3$, $H_4SiO_4$, $H_3BO_3$, $HClO_4$, $HBF_4$, $HSbF_5$, $HPF_6$, $H_2FO_3P$, $ClSO_3H$, $FSO_3H$, $HN(SO_2F)_2$, $HIO_3$, $BF_3$, $AlCl_3$, $Al(OTf)_3$, $FeCl_3$, $ZnCl_2$, $SnCl_2$, $CrCl_3$, $CeCl_3$, $ErCl_3$, formic acid, acetic acid, trifluoroacetic acid, lactic acid, levulinic acid, methanesulfinic acid, methanesulfonic acid, trifluoromethanesulfonic acid, bis(trifluoromethanesulfonyl)amine, benzoic acid, para-toluenesulfonic acid, 4-biphenylsulfonic acid, diphenyl phosphate and 1,1'-binaphthyl-2,2'-diyl hydrogen phosphate. Preferably, the acidic dehydration catalyst is chosen from HCl, $H_2SO_4$, $H_3PO_2$, $H_3PO_4$, $HNO_3$, $AlCl_3$, acetic acid, trifluoroacetic acid, methanesulfinic acid, methanesulfonic acid and trifluoromethanesulfonic acid.

The term "sugar" denotes a sugar containing 6 carbon atoms (hexoses), but this does not exclude the presence in the feedstock of sugars containing 5 carbon atoms (pentoses), in the form of oligosaccharides and monosaccharides. In particular, the term "sugar" denotes glucose or fructose, alone or as a mixture, sucrose, and also oligosaccharides such as cellobiose, maltose, cellulose or even inulin.

The sugar feedstock used may be sugar in solid form, or an aqueous sugar solution. By way of example, sucrose is generally produced in the form of a solid, while glucose or fructose, alone or as a mixture, are generally produced in the form of an aqueous solution (syrup), for example at 70% by weight of sugar.

The optional dehydration step is performed at a temperature of between 5° and 150° C., preferably between 6° and 140° C., preferably between 7° and 130° C. and more preferably between 8° and 120° C. Preferably, the optional dehydration step is performed at a pressure of between 1 and 0.001 MPa, preferably between 0.1 and 0.01 MPa. Depending on the pressure and temperature conditions, the reaction medium is above or below the bubble point of the mixture. The term "bubble point" denotes the pressure and temperature conditions under which the first gas bubbles are seen in a liquid. When the reaction medium is above the bubble point of the mixture, the vapor phase can be withdrawn from the reactor, optionally rectified, and condensed to form condensates which can be sent to an optional step f) for processing the water-DMSO mixtures.

Preferably, the acidic dehydration catalyst is introduced into the dehydration step in a mole ratio of the catalyst relative to the sugar feedstock, denoted Acid/Sugar, expressed as a molar percentage (mol %), of between 0.01 and 10 mol %, preferably between 0.05 and 8 mol %, preferably between 0.1 and 6 mol %, preferably between 0.2 and 5 mol %, more preferably between 0.3 and 4 mol % and very preferably between 0.5 and 3 mol %.

Advantageously, the effluent obtained on conclusion of the optional dehydration step comprises 5-HMF and DMSO. DMSO generally represents between 30% and 95% by weight of the effluent resulting from the dehydration step and treated in step a) of the process according to the invention, preferably between 40% and 90% by weight, preferably between 50% and 90% by weight, more preferably between 55% and 85% by weight.

5-HMF represents more than 1% by weight of the effluent resulting from the optional dehydration step and treated in step a) of the process according to the invention, preferably more than 10% by weight, preferably more than 15% by weight and preferably less than 50% by weight, preferably less than 40% by weight, more preferably less than 30% by weight.

Furthermore, said effluent from the optional dehydration step may contain water even before being mixed in step a) with the intermediate aqueous back-extract 9. Said water may be derived from the dehydration step: for example, water is formed during the dehydration reaction of sugar to 5-HMF (3 mol of water generated per mole of 5-HMF produced). This water may also have been introduced with the sugar, in the case where, for practical reasons, a sugar syrup, for example at about 70% by weight in water, is used. Advantageously, during the optional dehydration step, a water-DMSO mixture may be recovered in the vapor phase. Said water-DMSO mixture is advantageously sent to the optional step f). Thus, the effluent resulting from the optional dehydration step and introduced into step a) as feedstock 1 may contain water, in a proportion generally between 0.1% and 30% by weight, preferably between 0.1% and 15% by weight, more preferably between 0.1% and 10% by weight.

The effluent resulting from the optional dehydration step and introduced into step a) as feedstock 1 may also contain impurities, in particular humins. The term "humins" refers to all the undesirable polymeric compounds formed during the synthesis of 5-HMF. In particular, humins represent less than 30% by weight of the converted sugar feedstock, preferably less than 20% by weight.

The optional dehydration step may be performed according to various embodiments. Thus, the step may advantageously be performed batchwise or continuously. The addition of the sugar feedstock may be progressive (fed-batch) in the case of a batch process, or staged in different CSTR reactors (Continuously Stirred Tank Reactor) in series in the case of a continuous process. The process can be performed in a closed reaction chamber or in a semi-open reactor.

Mixing Step a)

The process according to the invention comprises a step a) of placing in contact the feedstock 1, optionally from the dehydration step, with at least a fraction of an intermediate aqueous back-extract 9, in order to obtain an aqueous mixture 3. Advantageously, the intermediate aqueous back-extract 9 is obtained from step c) of the process according to the invention.

Preferably, 5-HMF represents more than 1% by weight of the feedstock 1 introduced into step a) of the process according to the invention, preferably more than 10% by weight, preferably more than 15% by weight and preferably less than 50% by weight, preferably less than 40% by weight, more preferably less than 30% by weight.

Preferably, DMSO represents between 30% and 95% by weight of the feedstock 1 introduced into step a), preferably between 40% and 90% by weight, preferably between 50% and 90% by weight, more preferably between 55% and 85% by weight.

The feedstock 1 introduced into step a) may also contain water, in a proportion preferably between 0.1% and 30% by weight, preferably between 0.1% and 15% by weight and more preferably between 0.1% and 10% by weight.

Feedstock 1 may also optionally contain humins. Humins represent, in particular, less than 30% by weight of feedstock 1, preferably less than 20% by weight.

The intermediate aqueous back-extract 9 or the fraction of intermediate aqueous back-extract 9 is advantageously obtained from step c). It comprises water, DMSO and optionally 5-HMF. Advantageously, the intermediate aqueous back-extract 9 contains more than 60% by weight of water, preferably more than 70% by weight of water and preferably more than 80% by weight of water.

Advantageously, the aqueous mixture 3 obtained from step a) contains between 10% and 90% by weight of water, preferably between 20% and 80% by weight of water, more preferably between 40% and 75% by weight of water.

Preferably, step a) is performed at a temperature of from 0 to 60° C., preferably from 10 to 30° C. and generally at room temperature, i.e. between 18 and 25° C.

Step a) may optionally also be fed with an aqueous stream, for example with a fraction of the aqueous solvent used in the back-washing step c).

By increasing the water content during step a), for example by introducing at least a fraction of the intermediate aqueous back-extract 9, some of the humins that may be present in feedstock 1 can precipitate out. The mixture resulting from contact of said feedstock 1 with at least a fraction of the intermediate aqueous back-extract 9 can thus advantageously be subjected to a liquid-solid separation step, so as to obtain a liquid separated from suspended solid particles and a solid residue comprising humins and which is preferably eliminated from the process. Such an optional liquid-solid separation step thus allows precipitated humins to be removed. At least part of the liquid obtained is then advantageously sent to the liquid-liquid extraction step b), said part (or all) of the liquid advantageously sent to step b) corresponding to the aqueous mixture 3. This optional liquid-solid separation step is preferably performed at a temperature of between 0 and 60° C., preferably between 1° and 30° C., preferably between 15 and 25° C. and generally at room temperature (i.e. between 18 and 25° C.). The optional liquid-solid separation step may be performed via any method known to those skilled in the art, for instance with a filter press, a belt filter, a clarifier, a decanter or a centrifuge, for example a plate centrifuge. Preferably, the liquid-solid separation step is a filtration, preferably performed with a filter press.

Extraction Step b)

The process according to the invention comprises a step b) of liquid-liquid extraction of the mixture 3 obtained on conclusion of step a) in the presence of a stream 4 of extraction solvent, so as to produce an aqueous raffinate 5 and an intermediate organic extract 6.

The liquid-liquid extraction performed in step b) advantageously corresponds to washing the aqueous mixture with an organic extraction solvent. Preferably, the liquid-liquid extraction performed in step b) is a countercurrent extraction of the aqueous mixture 3 obtained in step a) with a stream of extraction solvent. This technique is well known to those skilled in the art. The extraction can be performed, for example, in a mixer-decanter array, in a column filled with random or structured packing, in a plug-flow column, or else in a stirred column.

The extraction step b) is advantageously performed at a temperature of between 0 and 60° C., preferably between 5 and 50° C., preferably between 1° and 40° C., more preferably between 15 and 30° C. and generally at room temperature (i.e. between 18 and 25° C.).

The proportion (weight/weight) of the stream of extraction solvent relative to the aqueous mixture 3 is preferably from 0.2 to 5, preferably between 1 and 3, more preferably between 1.5 and 2.5.

The extraction solvent is chosen from water-immiscible solvents, so as to form two liquid phases in particular in the back-washing step c) and in the back-extraction step d). This property is highly dependent on the relative proportion of the flow rates of feedstock, of back-extraction water and of extraction solvent used in the process.

In a nonlimiting manner, the extraction solvent is preferably chosen from the family of chlorinated organic solvents, ethers, esters, ketones and aromatic compounds. Preferably, the extraction solvent is a chlorinated solvent containing between 1 and 10 carbon atoms, noted below as C1-C10, an ether containing between 2 and 10 carbon atoms (C2-C10), an ester containing between 4 and 10 carbon atoms (C4-C10), a ketone containing between 3 and 10 carbon atoms (C3-C10), an aldehyde containing between 1 and 10 carbon atoms (C1-C10) or a C4-C10 aromatic compound. Preferably, the extraction solvent is chosen from dichloromethane, diethyl ether, diisopropyl ether, methyl ethyl ketone, methyl isopropyl ketone, methyl isobutyl ketone, thiophene, anisole and toluene. Very preferably, the extraction solvent is methyl isobutyl ketone.

Advantageously, the organic solvent streams produced in the subsequent steps may be advantageously recycled into the extraction step b). These organic solvent streams may contain impurities produced within the process. Advantageously, the organic solvent may be distilled periodically to avoid accumulation of said impurities.

According to a preferred embodiment of the invention, the stream of extraction solvent comprises, preferably consists of, a stream obtained from one of the steps of the process according to the invention. According to this preferred embodiment, the stream of extraction solvent comprises, preferably consists of, at least a fraction, preferably all, of an organic effluent, advantageously obtained from the back-extraction step d) and recycled to the extraction step b), the fraction or all of the organic effluent advantageously obtained from the back-extraction step d) optionally being able to be mixed with fresh extraction solvent, that is to say extraction solvent which is external to the process, to constitute the stream of extraction solvent introduced in step b).

The extraction step b) thus makes it possible to obtain, on the one hand, an aqueous stream depleted in 5-HMF, called aqueous raffinate 5, which contains a large proportion of the DMSO initially contained in the feedstock, and on the other hand an organic stream enriched in 5-HMF, called intermediate organic extract 6, which contains a large proportion of the 5-HMF, initially contained in feedstock 1, and the extraction solvent. This intermediate organic extract 6 may also contain DMSO. Preferably, said extract contains 5-HMF and DMSO in a 5-HMF/DMSO weight ratio of between 50/50 and 95/05, preferably between 55/45 and 90/10, preferably between 60/40 and 85/15 and more preferably between 65/35 and 80/20.

Advantageously, the intermediate organic extract 6 is sent to the back-washing step c).

Back-Washing Step c)

The process according to the invention comprises a step c) of back-washing, advantageously of the intermediate organic extract 6, with an aqueous solvent 7 so as to produce an intermediate aqueous back-extract 9 and an organic raffinate 8 comprising 5-HMF and an organic solvent. The organic solvent is in particular at least partly composed of extraction solvent and may optionally comprise DMSO, preferably in small amounts. Advantageously, the intermediate aqueous back-extract 9 is sent partly or totally into step a).

The introduction of an aqueous solvent in step c) is performed so as to perform the back-washing, according to the general knowledge of those skilled in the art. The introduction of the aqueous solvent is performed such that the amount of aqueous solvent is as low as possible in order to reduce costs, but sufficient to ensure a low DMSO weight content in the organic raffinate 8, preferably less than or equal to 20.0% by weight relative to the weight of 5-HMF, preferentially less than or equal to 15.0% by weight relative to the weight of 5-HMF, preferably between 0.01% and 15.0% by weight relative to the weight of 5-HMF, and preferably between 0.01% and 10.0% by weight relative to the weight of 5-HMF.

Advantageously, the aqueous back-washing solvent introduced in step c) comprises more than 95% by weight of water, preferably more than 98% by weight of water (100% being the maximum). The aqueous solvent may optionally comprise DMSO. The back-washing efficacy is all the higher the lower the amount of DMSO present in the aqueous back-washing solvent. Preferably, the aqueous solvent may comprise DMSO, preferably less than 1.0% by weight of DMSO, more preferably less than 0.1% by weight of DMSO. Advantageously, the aqueous back-washing solvent is derived from an optional step f) of treating water-DMSO mixtures produced within the process and/or from an optional concentration step e). In a preferred embodiment of the invention, the aqueous raffinate 5 composed of water and DMSO produced in step b) is treated, advantageously in an optional step f) which in particular comprises distillation. The water-rich distillate 7 obtained from this optional step f) is advantageously used as an aqueous back-washing solvent in step c); said water-rich distillate may also contain a residual amount of DMSO, preferably less than 1% by weight and preferably less than 0.1% by weight of DMSO. The residual amount of DMSO is proportionately lower the more efficiently the distillation of optional step f) is performed, in particular with a number of distillation stages greater than 10 and with suitable reboiling and reflux rates.

The back-washing step c) is advantageously a liquid-liquid extraction of the intermediate organic extract 6 obtained in step b) in countercurrent to the aqueous solvent 7 introduced. This technique is well known to those skilled in the art. The extraction can be performed, for example, in a mixer-decanter array, in a column filled with random or structured packing, in a plug-flow column, or else in a stirred column.

Step c) is generally performed at a temperature of between 0 and 60° C., preferably between 5 and 50° C., preferably between 1° and 40° C., more preferably between 15 and 30° C. and generally at room temperature (i.e. between 18 and 25° C.).

The mass ratio (weight/weight) of aqueous solvent relative to the intermediate organic extract 6 is preferably from 0.04 to 5, preferably between 0.07 and 3, more preferably between 0.1 and 1.

Step c) produces an aqueous stream enriched in DMSO, referred to as intermediate aqueous back-extract 9, preferably containing at least 60% by weight of water, preferably at least 80% by weight of water, and an organic raffinate 8 advantageously depleted in DMSO. Said intermediate aqueous back-extract 9 is advantageously sent, partly or preferably totally, to the mixing step a). The organic raffinate 8 obtained has a DMSO weight content preferably less than or equal to 20.0% by weight relative to the weight of 5-HMF, preferably less than or equal to 15.0% by weight relative to the weight of 5-HMF, preferably less than or equal to 5.0% by weight relative to the weight of 5-HMF, preferably less than or equal to 4.0% by weight relative to the weight of 5-HMF, preferably less than or equal to 3.0% by weight relative to the weight of 5-HMF.

According to the invention, the organic raffinate 8 produced in step c) is sent to the back-extraction step d).

Back-Extraction Step d)

The process according to the invention comprises a step d) of back-extraction of the organic raffinate 8 with an aqueous stream 10, so as to produce an aqueous back-extract 11 comprising 5-HMF and an organic effluent comprising the extraction solvent.

The aqueous back-extract 11 comprises 5-HMF preferably in a content of greater than or equal to 40% by weight, preferably greater than or equal to 50% by weight, relative to the entirety of the organic compounds, i.e. relative to the entirety of 5-HMF, DMSO and extraction solvent.

Advantageously, the process according to the invention produces an aqueous back-extract of 5-HMF of very high purity, containing a very small amount of humins, more particularly in trace amounts (that is, amounts which are not quantifiable or even not detected by HPLC liquid chromatography), or even being devoid of humins.

The aqueous stream 10 is introduced in step d) so as to implement the back-extraction in accordance with the general knowledge of those skilled in the art. The amount of the aqueous stream 10 introduced is adjusted so as to be as low as possible, to reduce costs, but sufficient to ensure effective back-extraction of the 5-HMF. With preference, at least 90% by weight, preferably at least 95% by weight, very preferably at least 98% by weight of the 5-HMF contained in the organic raffinate 8 which feeds step d) is back-extracted and is therefore present advantageously in the aqueous back-extract 11.

The back-extraction carried out in step d) is preferably a counter-current extraction of the organic raffinate 8 obtained on conclusion of step c) with an aqueous stream 10. This technique is well known to those skilled in the art. The extraction may be carried out, for example, in a battery of mixer-settlers, in a column filled with bulk or structured packing, in a pulsed column, or else in a stirred column.

The back-extraction step d) is preferably carried out at a temperature of between 0 and 60° C., preferably between 5 and 50° C., preferably between 1° and 40° C., preferably between 15 and 30° C., and more particularly at room temperature (i.e. between 18 and 25° C.).

The proportion (weight/weight) of the aqueous stream 10 relative to the organic raffinate 8 is preferably from 0.5 to 5, preferably between 1.0 and 3.0, preferably between 1.5 and 2.5. The amount of water in the aqueous stream added in the back-extraction step d) is preferably greater than the amount of water in the aqueous solvent added in the back-washing step c).

Advantageously, the aqueous stream 10 introduced in the back-extraction step d) comprises at least 95% by weight of water, preferably at least 98% by weight of water (100% being the maximum). The aqueous stream may optionally comprise DMSO. With preference, the aqueous stream comprises less than 1.0% by weight of DMSO, preferably less than 0.1% by weight of DMSO. Advantageously, the aqueous back-extraction solvent derives at least partly from an optional step f) of treatment of water-DMSO mixtures produced within the process and/or from an optional concentration step e). In one particular embodiment of the invention, the aqueous raffinate 5 composed of water and DMSO, produced in step b), is treated, advantageously in an optional step f) which comprises, in particular, a distillation, and the water-rich distillate obtained on conclusion of this optional step f) is advantageously used, at least partly, as the aqueous back-extraction stream in step d); the water-rich distillate obtained on conclusion of this optional step f) may also contain a residual amount of DMSO, preferably less than 1% by weight and with preference less than 0.1% by weight of DMSO.

On conclusion of the back-extraction step d), an aqueous solution comprising 5-HMF, corresponding to the aqueous back-extract 11, and an organic effluent comprising the extraction solvent are obtained. The process according to the invention thus produces an aqueous solution of 5-HMF of high purity, i.e. comprising a very small amount of humins, in the form of traces, or even free of humins.

The aqueous back-extract 11 produced in step d) may advantageously be sent, entirely or partly, to an optional concentration step e). The organic effluent in turn may be recycled, entirely or partly, to the extraction step b), to form at least a fraction of the extraction solvent stream 4.

Optional Back-Extract Concentration Step e)

Advantageously, the aqueous back-extract 11 may be concentrated to a concentrated aqueous solution 12 of 5-HMF by removal of an aqueous effluent 13.

Advantageously, the concentration of the aqueous solution, i.e. the removal of the aqueous effluent 13, is carried out by any method known to those skilled in the art, such as, for example, by evaporation or distillation or else reverse osmosis.

Advantageously, the concentrated aqueous solution 12 of 5-HMF obtained on conclusion of optional step e) comprises 5-HMF, in a content of greater than or equal to 30% by weight, preferably greater than or equal to 40% by weight, with preference greater than or equal to 50% by weight, and water. Preferably, the aqueous solution 12 of 5-HMF obtained on conclusion of optional step e) comprises not more than 90% by weight of 5-HMF, preferably not more than 85% by weight of 5-HMF and with preference not more than 80% by weight of 5-HMF, the balance to 100% being very advantageously essentially water. The aqueous solution 12 of 5-HMF obtained on conclusion of optional step e) therefore comprises very preferably at least 10% by weight of water, preferably at least 15% by weight of water, with preference at least 20% by weight of water, and very preferably up to 70% by weight of water, more particularly up to 50% by weight of water, especially up to 30% by weight of water. With preference, the DMSO content of concentrated aqueous solution 12 is very low, preferably less than 0.1% by weight, more preferably less than 500 ppm by weight and with preference less than 100 ppm by weight, relative to the weight of 5-HMF.

The aqueous effluent 13 obtained on conclusion of the optional concentration step e) is preferably composed essentially of water, preferably containing more than 95% by weight of water, preferably more than 98% by weight of water (100% being the maximum). The aqueous effluent 13 may advantageously be recycled to the back-washing step c) and/or the back-extraction step d).

Optional Step f) of Treating the Water-DMSO Mixtures

The process according to the invention may comprise an optional step f) of treating the water-DMSO mixtures generated by the steps of the process according to the invention, to produce a treated aqueous effluent (also known as distillate), which may be totally or partly used in the back-washing step c) and/or in the back-extraction step d). This step may also produce a DMSO-rich stream and an impurities stream.

The residual amount of DMSO in the treated aqueous effluent produced on conclusion of optional step f) is all the lower as distillation is performed in an efficient manner according to the knowledge of those skilled in the art.

The water-DMSO mixtures generated by the process denote in particular the aqueous raffinate 5 produced in step b) and optionally the water-DMSO mixture resulting from the optional step of dehydration of sugars to 5-HMF when the process incorporates such a step.

The water-DMSO mixtures generated by the process denote in particular the aqueous raffinate 5 produced in step b), and optionally the water-DMSO mixture resulting from the optional step of dehydration of sugars to 5-HMF when the process incorporates such a step.

Preferably, optional step f) of treating the water-DMSO mixtures involves a section for evaporating a water-DMSO mixture, to remove any impurities, in particular heavy impurities such as humins, followed by a distillation section.

The evaporation section is operated at a temperature preferably between 8° and 120° C., preferentially between 10° and 110° C., and preferably at a pressure between 0.002 and 0.020 MPa, preferentially between 0.005 and 0.010 MPa. Preferably, the evaporation section uses a Thin Film Evaporator (TFE).

The distillation section advantageously uses a distillation column or several separate items of equipment. Preferably, the distillation section of optional step f) is advantageously operated in a distillation column, at a column head temperature preferably between 25 and 60° C., preferentially between 45 and 55° C., for example about 50° C., preferably at a column bottom temperature of between 8° and 120° C., preferentially between 105 and 115° C., for example about 110° C., preferably at a pressure of between 0.001 and 0.05 MPa, preferentially between 0.005 and 0.02 MPa and more preferably between 0.008 and 0.012 MPa, and preferably with a reflux ratio of between 0.01 and 0.50, more preferably between 0.05 and 0.10.

Thus, the aqueous raffinate 5 produced in step b) and comprising water and DMSO and optionally the water-DMSO mixture recovered in the optional dehydration step are evaporated, then the gas phase is recovered and distilled, preferably under vacuum, so as to produce a DMSO-rich residue on the one hand and a water-rich distillate (corresponding to the treated aqueous effluent) on the other hand. The term "rich" here means more than 95% by weight, preferably more than 98% by weight. Part or all of the water-rich distillate, or treated aqueous effluent, may advantageously be recycled into step c) as aqueous solvent to perform the back-washing step and/or into the back-extraction step d) as aqueous stream. The water-rich distillate may also be totally or partly recycled as water introduced into step a).

The DMSO-rich residue may advantageously be introduced into the optional dehydration step, either directly or after distillation, allowing any heavy products that may accumulate to be removed.

The examples and FIGURES appended below illustrate the invention without limiting its scope.

BRIEF DESCRIPTION OF FIGURES

FIG. 1 illustrates an embodiment of the process according to the invention. The feedstock 1) containing 5-HMF, DMSO and humins is sent to the mixing step a) and placed in contact with the intermediate aqueous back-extract 9 from step c), after which the precipitated humins 2 are removed from the mixture by liquid-solid filtration. The aqueous mixture 3 obtained on conclusion of step a) is sent to extraction step b) and placed in contact with an extraction solvent 4 recycled from step d), so as to extract the 5-HMF from the aqueous mixture using the extraction solvent and obtain an aqueous raffinate 5 and an intermediate organic extract 6. The intermediate organic extract 6 is placed in contact with an aqueous solvent 7 in the back-washing step c). The organic raffinate 8 obtained is sent to the back-extraction step d) and placed in contact with an aqueous stream 10 so as to extract the 5-HMF from the water and form an aqueous stream 11. The aqueous stream 11 is then advantageously concentrated in step e) to obtain an aqueous solution 12 of 5-HMF and an aqueous effluent 13.

EXAMPLES

Example 1: Process According to the Invention

Example 1 presents the process and the results obtained by an example of the process according to the embodiment of the invention of FIG. 1.

An acid catalyst, methanesulfonic acid, is mixed with DMSO, such that the mole ratio with the sugar feedstock (catalyst/sugar feedstock) is 1 mol %, and they are brought to a temperature of 120° C. Fructose is introduced in the form of an aqueous solution, at 70% by weight of sugar (syrup), in a DMSO/fructose mass ratio of 2.3. The pressure is maintained at 0.035 MPa. Under these pressure and temperature conditions, the reaction medium is above the bubble point of the mixture, so the vapor phase can be withdrawn from the reactor, and condensed to form the condensates. The sugar dehydration step is performed batchwise, by addition of feedstock progressively over a 2-hour period. The reaction medium is maintained at the temperature and pressure indicated above for a further 2 h after the end of addition.

The effluent resulting from the dehydration step contains 74% by weight of DMSO, 21% by weight of 5-HMF and 3% by weight of water, giving a molar yield of 5-HMF relative to engaged fructose of 81%. Polymeric compounds (called humins) which are soluble in the reaction medium were formed in an amount of 5% by weight. During this dehydration step, a water-DMSO mixture is recovered in the vapor phase. Said water-DMSO mixture has a composition of 32% by weight of DMSO and 68% water. This water-DMSO mixture is distilled under vacuum to produce water containing only traces of DMSO.

The liquid effluent from the dehydration step corresponding to feedstock 1 is engaged in a step a) of placing in contact with water, at room temperature, so as to obtain a mixture which contains a DMSO/water mass ratio equal to 1.

The mixture from step a) is subjected to a liquid-solid separation step, on a Büchner filter equipped with a polypropylene gauze filter with a pore size of 10 μm. This liquid-solid separation step is performed at room temperature. During the liquid-solid separation step, 7.5 g of a "humins" solid residue/kg of filtered mixture are recovered, along with a homogeneous liquid phase corresponding to aqueous mixture 3. Aqueous mixture 3 is composed of 43% by weight of DMSO, 12% by weight of 5-HMF, 43% by weight of water, and comprises impurities (about 2% by weight of humins).

The aqueous mixture 3 resulting from step a) is subjected to a countercurrent liquid-liquid extraction step b) in a stirred glass column (ECR or Kühni type) comprising eight sections 225 mm high and with an inside diameter of 32 mm, and also a lower decanter and an upper decanter. The useful height is about 1.8 m and the total column height is 2.60 m. The total volume is about 3 liters. The organic extraction solvent is methyl isobutyl ketone (MIBK). The aqueous mixture 3 is introduced into the upper part of the device and dispersed in the ascending organic phase. The column inlet flow rates are set at 2.2 kg/h for the DMSO-water phase and 4.1 kg/h for the organic solvent. The proportion (weight/weight) of MIBK solvent is 1.9 relative to the aqueous mixture 3 resulting from step b). The temperature is 20° C. and the stirring speed is 300 rpm.

On conclusion of step b), a 5-HMF-depleted aqueous raffinate 5 is recovered, containing about 48% by weight of water, 48.5% by weight of DMSO, 0.4% by weight of 5-HMF, 1.8% by weight of MIBK, and humin impurities, and an intermediate organic extract 6 enriched in furan compounds containing 2.8% by weight of DMSO, 5.9% by weight of 5-HMF (a 5-HMF/DMSO weight ratio of about 68/32) and 91.3% by weight of MIBK. The extraction yield is 97% for 5-HMF and 13% for DMSO.

The intermediate organic extract 6 resulting from liquid-liquid extraction step b) is subjected to a back-washing step c) in the same type of extraction device (ECR or Kühni type stirred column). Said organic extract is dispersed in the descending pure water phase at 21.5° C. The column inlet flow rates are set at 5 kg/h for the organic extract and 1.5 kg/h for the aqueous phase. The proportion (weight/weight) of water introduced as aqueous back-washing solvent relative to the intermediate organic extract is 0.3.

On conclusion of back-washing step c), a DMSO-enriched intermediate aqueous back-extract 9 is recovered, containing 86% by weight of water, 7% by weight of DMSO, 5% by weight of 5-HMF and 2% by weight of MIBK, and an organic raffinate 8, containing 0.092% by weight of DMSO, 4.3% by weight of 5-HMF (i.e. 2.1% by weight of DMSO relative to the weight of 5-HMF) and 88% by weight of MIBK, giving a back-washing yield of 27% by weight for 5-HMF and 95% by weight for DMSO.

The organic raffinate 8 resulting from back-washing step c) is subjected to a liquid-liquid back-extraction step d) in the same type of extraction device (ECR or Kühni type stirred column). Said organic raffinate 8 is dispersed in the descending pure water phase, at 21.5° C. and 300 rpm. The column entry flow rates are set at 2.2 kg/h for the organic raffinate and at 4.4 kg/h for the aqueous phase. The proportion (weight/weight) of water introduced in step d) relative to the organic raffinate 8 is 2.

On conclusion of back-extraction step d), the following are recovered: an organic raffinate depleted in 5-HMF, containing 0% by weight of DMSO, 0.15% by weight of 5-HMF and 96% by weight of MIBK, and an aqueous solution 11 enriched in 5-HMF, containing 0.045% by weight of DMSO, 2.0% by weight of 5-HMF, 1.6% by weight of MIBK and approximately 96.4% by weight of water. The extraction yield is 97% for the 5-HMF. The aqueous solution 11 does not comprise humins or comprises them only in the form of traces (not detected by liquid chromatography or HPLC).

The aqueous solution 11 is subsequently concentrated by distillation to give a concentrated aqueous solution 12 comprising 78% by weight of 5-HMF and an aqueous effluent 13.

The invention claimed is:

1. A process for producing an aqueous solution of 5-hydroxymethylfurfural (5-HMF), said process comprising:

a) placing a feedstock (1) comprising 5-HMF and dimethyl sulfoxide (DMSO) in contact with at least a fraction of an intermediate aqueous back-extract (9) obtained from c) to obtain at least one aqueous mixture (3), b) subjecting the aqueous mixture (3) obtained on conclusion of a) to liquid-liquid extraction in the presence of a stream (4) of extraction solvent to produce an aqueous raffinate (5) and an intermediate organic extract (6), c) back-washing the intermediate organic extract (6) with an aqueous solvent (7) to produce the intermediate aqueous back-extract (9) and an organic raffinate (8) which comprises 5-HMF and an organic solvent, and d) subjecting the organic raffinate (8) obtained on conclusion of c) to liquid-liquid back-extraction with an aqueous stream (10) to produce an organic effluent and an aqueous back-extract (11).

2. The process as claimed in claim 1, wherein the back-extraction in d) is a counter-current extraction of the organic raffinate (8) obtained on conclusion of c) with the aqueous stream (10).

3. The process as claimed in claim 1, wherein d) is carried out at a temperature of between 0 and 60° C.

4. The process as claimed in claim 1, wherein, in d), the weight proportion of the aqueous stream (10) relative to the organic raffinate (8) is from 0.5 to 5.

5. The process as claimed in claim 1, wherein the amount of water in the aqueous stream (10) added in the back-extraction d) is greater than the amount of water in the aqueous solvent (7) added in the back-washing c).

6. The process as claimed in claim 1, wherein the aqueous stream (10) introduced in the back-extraction d) comprises at least 95% by weight of water.

7. The process as claimed in claim 1, further comprising e) concentrating the aqueous back-extract (11) obtained from d) by removal of an aqueous effluent (13), to produce a concentrated aqueous solution (12) comprising 5-HMF.

8. The process as claimed in claim 1, wherein the extraction solvent is chosen from dichloromethane, diethyl ether, diisopropyl ether, methyl ethyl ketone, methyl isopropyl ketone, methyl isobutyl ketone, thiophene, anisole, and toluene.

9. The process as claimed in claim 1, wherein, in the back-washing c), the weight ratio of aqueous solvent (7) relative to the intermediate organic extract (6) is from 0.04 to 5.

10. The process as claimed in claim 1, further comprising, upstream of a), dehydrating sugars to 5-HMF.

11. The process as claimed in claim 1, further comprising f) treating the water-DMSO mixtures produced within the process, to produce a treated aqueous effluent, which is used totally or partly in the back-washing c), and/or in e).

12. The process as claimed in claim 1, wherein d) is carried out at a temperature of between 15 and 30° C.

13. The process as claimed in claim 1, wherein, in d), the weight proportion of the aqueous stream (10) relative to the organic raffinate (8) is between 1.0 and 3.0.

14. The process as claimed in claim 1, wherein, in d), the weight proportion of the aqueous stream (10) relative to the organic raffinate (8) is between 1.5 and 2.5.

15. The process as claimed in claim 1, wherein the aqueous stream (10) introduced in d) comprises at least 98% by weight of water.

16. The process as claimed in claim 1, wherein the extraction solvent is methyl isobutyl ketone.

17. The process as claimed in claim 1, wherein, in c), the weight ratio of aqueous solvent (7) relative to the intermediate organic extract (6) is between 0.07 and 3.

18. The process as claimed in claim 1, wherein, in c), the weight ratio of aqueous solvent (7) relative to the intermediate organic extract (6) is between 0.1 and 1.

19. The process as claimed in claim 1, further comprising, upstream of a), dehydrating sugars to 5-HMF by placing a sugar feedstock comprising one or more sugars in contact with DMSO and an acidic dehydration catalyst at a temperature of between 5° and 150° C.

20. The process as claimed in claim 1, further comprising, upstream of a), dehydrating sugars to 5-HMF by placing a sugar feedstock comprising one or more sugars in contact with DMSO and an acidic dehydration catalyst at a temperature of between 5° and 150° C. and at a pressure of between 1 and 0.001 MPa.

21. The process as claimed in claim 1, further comprising, upstream of a), placing a sugar feedstock comprising one or more sugars in contact with DMSO and an acidic dehydration catalyst to dehydrate the sugars to 5-HMF.

* * * * *